(12) United States Patent
Somekh et al.

(10) Patent No.: US 7,142,308 B2
(45) Date of Patent: Nov. 28, 2006

(54) MICROSCOPY

(75) Inventors: Michael Geoffrey Somekh, Wollaton (GB); Chung Wah See, Leicester (GB)

(73) Assignee: The University of Nottingham, Nottingham (GB)

( * ) Notice: Subject to any disclaimer, the term of this patent is extended or adjusted under 35 U.S.C. 154(b) by 282 days.

(21) Appl. No.: 10/297,076

(22) PCT Filed: May 30, 2001

(86) PCT No.: PCT/GB01/02399

§ 371 (c)(1),
(2), (4) Date: Jun. 20, 2003

(87) PCT Pub. No.: WO01/92858

PCT Pub. Date: Dec. 6, 2001

(65) Prior Publication Data

US 2004/0100636 A1 May 27, 2004

(30) Foreign Application Priority Data

May 30, 2000 (GB) ................................ 0013139.1

(51) Int. Cl.
*G01B 9/02* (2006.01)
(52) U.S. Cl. .................................... 356/450
(58) Field of Classification Search ................ 356/450, 356/451, 453, 456, 484, 491, 497, 498
See application file for complete search history.

(56) References Cited

U.S. PATENT DOCUMENTS

| 5,141,311 | A |   | 8/1992 | Hickel et al. |
| 5,237,392 | A |   | 8/1993 | Hickel et al. |
| 5,442,448 | A |   | 8/1995 | Knoll |
| 6,594,011 | B1 | * | 7/2003 | Kempen ........................ 356/369 |

FOREIGN PATENT DOCUMENTS

JP    2000055805 A    9/2000

OTHER PUBLICATIONS

Somekh M G et al., "High-Resolution Scanning Surface-Plasmon Microscopy", Applied Optics, Dec. 1, 2000, Opt. Soc. America, USA, vol. 39, No. 34, pp. 6279-6287, XP001008759, ISSN: 0003-6935, Figures 1, 2, 6.

Somekh M G et al., "Optical V(z) for High-Resolution 2 Pi Surface Plasmon Microscopy", Optics Letters, Jun. 1, 2000, Opt. Soc. America, USA, vol. 25, No. 11, pp. 823-825, XP001013062, ISSN: 0146-9592, Figures 1, 2.

Kano H et al., "Locally Excited Surface-Plasmon-Polaritons for Thickness Measurement of LBK films", Optics Communications, North-Holland Publishing Co. Amsterdam, NL, vol. 153, No. 4-6, Aug. 1, 1998, pp. 235-239, XP004146356, ISSN: 0030-4018, Figures 1, 4.

(Continued)

*Primary Examiner*—Hwa (Andrew) Lee
*Assistant Examiner*—Michael A. Lyons
(74) *Attorney, Agent, or Firm*—Michael Best & Friedrich LLP

(57) ABSTRACT

A method and apparatus for analyzing a sample are provided. The method can include the steps of: (i) irradiating the sample with a beam of radiation in which at least some of the radiation results in the excitation of surface waves, (ii) exciting surface waves which are confined to an area having a principal dimension comparable to the wavelength of the surface waves, (iii) detecting radiation which includes radiation produced by the surface waves, and (iv) analyzing the detected radiation.

41 Claims, 5 Drawing Sheets

OTHER PUBLICATIONS

Hickel W et al., "Surface Plasmon Optical Characterization of Lipid Monolayers at 5 Mum Lateral Resolution", Journal of Applied Physics, American Institute of Physics, New York, US, vol. 67, No. 8, Apr. 15, 1990, pp. 3572-3575, XP002032127, ISSN: 0021-8979, Figure 2.

Zayats, A V et al., "Observation of Localized Plasmonic Excitations in Thin Metal Films with Near-Field Second-Harmonic Microscopy" Optics Communications, Oct. 1, 1999, Elsevier, Netherlands, vol. 169, No. 1-6, pp. 93-96, XP001013180, ISSN: 0030-4018, p. 95, col. 1.

Aust E et al., "Electro-Optic Characterization of Polymeric Materials for Integrated Optics" Nonlinear Optical Properties of Organic Materials VI, San Diego, CA, USA, 13-16, Jul. 1993, vol. 2025, pp. 255-265, XP001008696, Proceedings of the SPIE—The International Society for Optical Engineering, 1993, USA, ISSN: 0277-786X, pp. 255-256, pp. 261-263.

Berger C E H et al., "Resolution in Surface Plasmon Microscopy" Review of Scientific Instruments, American Institute of Physics, New York, NY, US, vol. 65, No. 9, Sep. 1, 1994, p. 2829-2836, XP000469214, ISSN: 0034-6748, Figures 1,3,9,10.

Velinov T et al., "Direct Far-Field Observation of Surface-Plasmon Propagation by Photoinduced Scattering", Applied Physics Letters, Dec. 20, 1999, AIP, USA, vol. 75, No. 25, pp. 3908-3910, XP001008880, ISSN: 0003-6951, Figure 1.

\* cited by examiner

MICROSCOPY

This invention relates to improvements in and relating to microscopy, particularly surface wave microscopy.

Surface wave microscopy systems are known. For example, systems employing a particular type of surface wave, surface plasmons (SPs), are already in use. These often make use of the so-called Kretschmann configuration, where a metal layer, typically of thickness 50 nm, is deposited on the hypotenuse of a prism, which is illuminated from one of the other sides. The interest in SPs lies in the fact that their propagation properties are very strongly affected by the presence of and the properties of dielectric materials deposited on or attached to the metal surface. For instance, an atomic layer of dielectric will perturb the angle at which SPs are excited to a measurable extent. This property has led to the widespread use of SPs microscopy systems as chemical and biological sensors.

A problem with existing SP microscopy systems is their limited lateral (i.e. along the sample surface) resolution. Attempts have been made to obtain good lateral resolution using conventional far field optics. However the lateral resolution obtained with even this approach is rather poor. The usual explanation for the poor resolution is that the SPs when excited spread over a large area of the sample surface, since their decay length is of the order of tens of microns. This means that it is rather difficult to improve the lateral resolution to a value much better that this value. Systems which rely on the microscopic examination of scattered light from the Kretschmann configuration therefore achieve rather poor resolution, and the practical limit appears to be little better than 3 μm even when special measures are taken. The only methods able to achieve better resolution using SPs are probe microscopy techniques, where the evanescent field of the SPs is detected using a proximal probe. These techniques involve probing a sample in very close proximity, making them unsuitable in many applications. The sample is probed from the dielectric side thereof. However, it is desirable to remotely probe the sample from the metal side thereof, and at the same time to achieve good lateral resolution. This is so for SP and other surface wave microscopy systems.

According to a first aspect of the present invention there is provided a method of analysing a sample using a microscopy apparatus comprising the steps of:

(i) irradiating the sample with a beam of radiation in which at least some of the radiation is incident on the sample at an angle or angles which results in the excitation of surface waves,
(ii) exciting surface waves at a surface of the sample, which surface waves are confined to an area having a principal dimension which is comparable to the wavelength of the surface waves,
(iii) detecting radiation which includes radiation produced by the surface waves, and
(iv) analysing the detected radiation to obtain information about the sample.

The analysing will often be imaging the sample, but other forms of analysing are also possible. The maximum intensity of the surface waves may thus be achieved at a focus. The size of the focus, and therefore the resolution achieved by this method, is determined by the wavelength of the surface waves rather than their propagation length, i.e. it is diffraction limited rather than propagation length limited. The size of the focus in the plane of the sample surface may not be equal to the size of the focus normal to the plane of the sample surface. The diameter of the focus in the plane of the sample surface is preferably 1 μm or less.

The surface waves may be confined to such an area by restricting the area over which they are excited. This may be achieved by placing the sample at the focal plane of the microscopy apparatus. The sample will therefore be irradiated by a beam of radiation of confined area. Alternatively a mask may be provided for the illuminating beam.

The surface waves may be confined to such an area by allowing them to come to a focus. The surface waves may be excited over a substantially circular or elliptical area of the sample surface, and allowed to come to a focus at substantially the centre of the area. The centre of the area preferably coincides with the axis of the microscopy apparatus. Excitation over a substantially circular or elliptical area may be achieved by placing the sample at the focal plane of the microscopy apparatus.

The surface waves may be excited over an annulus of the sample surface, and allowed to come to a focus at substantially the centre of the annulus. The centre of the annulus preferably coincides with the axis of the microscopy apparatus. Excitation over an annulus may be achieved by irradiating the sample with an annular beam of radiation. This may be achieved by using a radiation source which produces an annular beam of radiation. This may be achieved by irradiating the sample through an objective lens in the microscopy apparatus which has a ring placed in the back focal plane thereof. The ring may be positioned such that irradiation of the sample takes place over a range of angles which includes the range of angles for excitation of surface waves, but substantially excludes other angles.

Excitation over an annulus may be achieved by placing the sample at a position off the focal plane of the microscopy apparatus. A circle of radiation will then be incident on the sample surface, and as surface waves are excited by radiation incident on the sample at a particular range of angles, only an annulus of the circle of radiation will excite surface waves. The range of angles will depend on the material of the sample being analysed. The range of angles may be 1 or 2 or 3 degrees, or more or less than these values. The annulus may have an internal or external diameter of the order of several microns.

By placing the sample at a position off the focal plane of the microscopy apparatus, the background signal which will be present is reduced, and the contribution of the radiation generated by the surface waves in the detected radiation will be increased.

The position of the sample off the focal plane of the microscopy apparatus may be varied. This may be achieved using sample moving means. For example, the sample could first be placed just off the focal plane and moved in incremental steps away from the focal plane. Alternatively, the sample could be first placed at a distance from the focal plane and moved in incremental steps towards the focal plane. These are commonly referred to as defocussing the sample, and the distance of the sample off the focal plane is referred to as the defocus, reference z. Preferably the sample is placed above the focal plane of the apparatus, and is moved away from or towards the focal plane. Variation of the defocus z will allow changes in the contrast between different features of the sample to be analysed. Variation of the defocus z may be used to determine the optimum defocus at which the sample should be positioned for analysis. Of course, the sample could be stationery and at least part of the microscopy apparatus moved: relative movement is what is required. In some embodiments we may move the objective lens (and leave the body of the microscope stationary).

The method may comprise using a microscopy apparatus which comprises a means to excite surface waves. This may comprise a fluid, e.g. oil, immersion objective lens. The sample may be placed at the focal plane of the objective lens, or off the focal plane of the objective lens.

The method preferably allows excitation of the surface waves and the detection of the radiation generated by the surface waves from one side of the sample. The method is preferably a far field method, i.e. the excitation of the surface waves and the detection of the radiation generated by the surface waves is achieved from the far field. This avoids placing a probe in close proximity to the sample which may perturb the measurement, a disadvantage of probe techniques.

A sample may be examined away from its sample side (reducing interference) or away from its dielectric side: the technique is not restricted to examining one side only of a sample: in particular we can examine the non-sample side, with inherent benefits.

We can also examine a sample at greater distances than can some other techniques: for example a microscope lens/sample separation of the order of 100 microns or so may be typical (e.g. 100 μm, 200 μm, etc.).

The sample may be irradiated with a beam of radiation from a laser. The laser may be a continuous wave laser, for example a 633 nm HeNe laser. The laser may be a pulsed laser, for example a titanium sapphire laser.

The sample may be scanned using scanning means to provide information about a number of points thereof. The method may comprise using mechanical scanning means. The method may comprise using mirror scanning means.

The method may comprise using a microscopy apparatus having a widefield configuration. Information about a number of points of the sample may therefore be obtained without the need to employ any scanning technique. This method may comprise passing a beam of radiation through a diffuser, and using the resultant beam to irradiate the sample and a reference mirror each with a speckle pattern. The radiation from these may be interfered, preferably at the image plane. The interference signal will relate to the strength of correlation between the two speckle patterns. The diffuser may be rotated, to ensure that the average value of the correlation is obtained so that speckle noise is averaged. The interference signal may be extracted from the background signal using a phase stepping algorithm. Such a wide-field imaging method will provide diffraction limited resolution.

Alternatively, use of a reference beam may be dispensed with, and the interference conditions between different parts of the radiation irradiating the sample may be changed. This method may comprise using a conventional optical microscope with an oil illumination objective lens, and critically illuminating the sample. In critical illumination, each point of illumination is mutually incoherent, whereas in the back focal plane of the lens the field consists of a spectrum of plane waves coherent within themselves but incoherent between each other. The imaging process may thus consist of coherently adding each of these plane waves to a point in the image plane. The sample is preferably placed at a position off the focal plane of the objective lens, preferably just off the focal plane of the lens, i.e. the sample is slightly defocused. This imposes a phase shift, so that the radiations generated by the excitation of surface waves add in phase. The method may further comprise filtering the input distribution in the back focal plane, by only allowing incident angles close to normal incidence and those within a few degrees of the angles required to excite surface waves. This will enhance the contrast of the surface waves further. A spatial light modulator in the back focal plane may be used to change the relative phase of the light incident close to normal incidence and that involved with excitation of surface waves. This will allow a modified phase stepping algorithm to be used to recover the surface wave contribution separately. A CCD camera of limited dynamic range may be used to detect the radiation generated by the surface waves. When this is the case, the defocusing, spatial filtering and phase stepping are important stages in making a practical full field surface wave microscope. These processes increase the surface wave signal, reduce the background and remove the background signal. The processing ensures that the surface wave signal has a good signal to noise ratio, but it also very important to ensure that the background signal is not so large to ensure that the available grey levels of the CCD camera are not absorbed by a dominant background signal. This method could ultimately offer better performance in terms of stability and simplicity.

The sample may comprise a conducting material, e.g. a metal layer, with one or more dielectric materials deposited on or attached to a surface of the conducting material. The surface waves may be excited in a surface of the conducting material. For generalised surface waves, additional layers may be used to support the surface waves. The information obtained about the sample may comprise information on the presence and/or composition and/or function of the one or more dielectric materials. The one or more dielectric materials may comprise a biological or chemical or pharmaceutical material or materials.

Two or more of the surface waves may together produce fluorescence in the sample. The surface waves are photons and this is known as multi-photon excitation and relies on the co-operative excitation by a number of photons which act together to excite a carrier from the ground state to an excited state across an energy gap which is greater than the energy of the individual photons but smaller than the total energy of the co-operating photons. Two-photon excitation will generally be the dominant process. When the carrier returns to the ground state it emits fluorescent radiation, the energy of which is generally greater than the energy of the individual exciting photons. Multi-photon excitation therefore relies on excitation with photons having a long wavelength, for example of the order of 800 nm, producing fluorescent radiation having a shorter wavelength, for example of the order of 400 to 500 nm. The fluorescent radiation will provide information about the sample. The detected radiation may include fluorescent radiation from the sample. One or more characteristics of this radiation may be detected and subsequently analysed. The one or more characteristics may comprise, for example, the number or the energy spectrum of the fluorescent photons.

The strength of two-photon emission will be proportional to the square of the intensity of the excited surface waves. In general, the strength of the emission is proportional to the intensity to the power of the order of the process (e.g. the square of the intensity for a two photon process, the cube of the intensity for a three photon process). As, in this method, the surface waves come to a focus, their intensity at the focus will be enhanced, and therefore the multi-photon excitation at the focus will be enhanced. In addition, when the sample comprises a metal layer with one or more dielectric materials deposited on or attached to a surface thereof, the surface wave excitation will be enhanced. Multi-photon excitation using surface waves will therefore be very suitable for the examination of interfaces and surface properties.

When the sample comprises a metal layer with one or more dielectric materials deposited on or attached to a surface thereof, the metal may be chosen to be at least substantially opaque to the radiation used to irradiate the sample. This is a condition for the effective excitation and propagation of surface waves. The metal may also be substantially transparent to the fluorescent radiation from the sample. This will allow enhanced transmission of the fluorescent radiation through the sample. The sample may then be irradiated from and fluorescent radiation detected from the same surface thereof. A metal which satisfies this is gold. This is substantially opaque to radiation having a wavelength of approximately 800 nm and substantially transparent to radiation having a wavelength of approximately 500 nm or less.

The sample may have one or more fluorophores added to it. The detected fluorescent radiation will be affected by the presence of the fluorophores, and will provide information about the sample. For example, the presence of the fluorophores may allow the composition or the function of the sample to be analysed.

Multi-photon excitation may be achieved by surface waves which are excited over a substantially circular or elliptical area of the sample surface by, for example, placing the sample at the focal plane of the microscopy apparatus, and which come to a focus at substantially the centre of the area. Multi-photon excitation may be achieved by surface waves which are excited over an annulus of the sample surface. This may be achieved by placing the sample at a position off the focal plane of the microscopy apparatus, and which come to a focus at substantially the centre of the annulus. This may be achieved by placing a ring in the back focal plane of the apparatus. This may be achieved by controlling the polarisation of the radiation used to irradiate the sample.

The method may comprise using a microscopy apparatus which comprises a fluid, e.g. oil, immersion objective lens. The sample may be placed at the focal plane of the objective lens, or off the focal plane of the objective lens. A proportion of the beam of radiation used to irradiate the sample may be reflected from the sample surface. The fluorescent radiation from the sample may be weaker than this reflected radiation. The method may comprise at least partially blocking radiation reflected from the sample. This may be achieved by using blocking means such as an interference filter.

The sample may be irradiated with a beam of radiation from a pulsed laser. Such a laser will have large peak powers and will therefore enhance the strength of multi-photon excitation. The pulsed laser may comprise a titanium sapphire laser.

The method may comprise exciting harmonic surface waves. These may comprise second or third or higher harmonic surface waves. Second harmonic surface waves will have half the wavelength of the radiation used to irradiate the sample, third harmonic surface waves will have one third of this wavelength etc. The detected radiation may comprise radiation produced by the harmonic surface waves. The radiation used to irradiate the sample will generate surface waves therein, and non-linearities in the sample, particularly regions at the surface where the symmetry is broken, will lead to generation of second (or higher) harmonic surface waves. Some of these surface waves may be detected, for example they may return back from the sample through an objective lens of the apparatus to a detector thereof. High intensity of the radiation used to irradiate the sample close to the optical axis, will ensure that most of the harmonic surface waves are generated in this region.

The radiation produced by the harmonic surface waves may be combined with a reference beam of radiation. These may be combined by causing them to interfere with each other. The method may comprise using an apparatus provided with or configured as an interferometer to achieve interference of these radiations. The reference beam of radiation should be coherent with the radiation produced by the harmonic surface waves. This may be achieved by splitting the beam of radiation used to irradiate the sample and passing a part thereof though a non-linear crystal. The radiation produced by the harmonic surface waves and the radiation from the crystal may then interfered. Interference of the two radiations may be obtained using a heterodyne interferometer. This may employ a Bragg cell. Interference of the two radiations may be obtained by using a phase stepping approach.

This method will give contrast not accessible to conventional linear imaging, being particular sensitive to the properties of interfaces, where symmetry is broken. The high sensitivity conferred by the interference configuration will enable very weak harmonic surface wave radiation to be detected in a relatively simple manner. Interference can also allow the complex susceptibility of the sample to be measured, which could give important information on the internal relaxation processes in the sample under investigation, particularly biological samples.

The method may comprise using a beam of radiation to irradiate the sample which has been produced by a pulsed laser, which preferably has a high peak power. The pulsed laser may comprise a titanium sapphire laser.

Detection of the radiation produced by the harmonic surface waves can also be achieved without use of the reference beam. i.e. without use of an interferometer. Information about the complex quantities of the sample will not then accessible and different detection methodologies are required, but this method is very attractive because of its relative simplicity. This method may also involve two-photon excitation of fluorescent radiation. Both the radiation produced by second harmonic surface waves and the fluorescent radiation may be detected simultaneously, by detecting the radiations at different wavelengths. The radiation produced by the second harmonic surface waves will be emitted at half the wavelength of the radiation used to irradiate the sample. The fluorescent radiation will be emitted at a wavelength slightly greater than half the wavelength of the radiation used to irradiate the sample. The two radiations may be separated with wavelength selective components such as, for example, dichroic mirrors or interference filters.

The surface waves which are excited may be surface plasmons. Surface plasmons are only excited by p-polarised radiation. The polarisation state of the radiation incident on the sample will depend on the polarisation state of the radiation incident on the back focal plane of the apparatus. The radiation incident on the back focal plane may be linearly polarised (some lasers emit linearly polarised light, but we may include polarisation controlling optics, e.g. linear polariser). In this case, the polarisation of the radiation incident on the sample will vary between pure p-polarisation through a combination of p and s polarisation to pure s-polarisation as the azimthuthal angle is changed. The consequence of this is that the strength of the p-polarisation of the radiation in the annulus of radiation which is incident on the sample at such an angle or angles to excite SPs will vary, being strongest in a direction parallel with the direction of polarisation of the radiation incident on the back focal plane, and weakest in a direction normal to this. The radiation incident on the back focal plane may be circularly polarised. In this case, the strength of the p-polarisation of the Radiation in the annulus of radiation which is incident on the sample at such an angle or angles to excite SPs does not vary. The radiation incident on the back focal plane may be radially polarised, i.e. may be polarised in a direction along the radius of the back focal plane. In this case, excitation of SPs will be enhanced. The radiation incident on the back focal plane may be linearly polarised such that the phase of the radiation differs by 180 degrees in different semicircles thereof. This allows enhanced SP excitation at the centre of the annulus of radiation which is incident on the sample at such an angle or angles to excite SPs, when the sample is defocused.

The detected radiation may include radiation produced by the surface plasmons. The detected radiation may include radiation irradiated from the sample surface which has excited surface plasmons therein. One or more characteristics of this radiation may be detected and analysed. The one or more characteristics may comprise the phase and/or amplitude of the radiation.

The detected radiation may further include radiation irradiated from the sample surface which has not excited any surface plasmons therein. One or more characteristics of this radiation may be detected and analysed. The one or more characteristics may comprise the phase and/or amplitude of the radiation.

The radiation irradiated from the sample surface which has excited surface plasmons therein and the radiation irradiated from the sample surface which has not excited any surface plasmons therein may be combined with a reference beam of radiation. These radiations and the reference beam of radiation may be combined by allowing them to interfere with each other. The method may comprise using a microscopy apparatus provided with or Configured as an interferometer to achieve interference of these radiations. In general, the radiation irradiated from the sample surface which has excited surface plasmons therein and the radiation irradiated from the sample surface which has not excited any surface plasmons therein are spatially distinct. The reference beam of radiation may be caused to overlap and therefore interfere with both these radiations. The beam of radiation for irradiating the sample and the reference beam of radiation may be produced from the same radiation source. The overall interference signal generated by the interference of the radiations and the reference beam of radiation may be analysed to obtain information about the sample. Particularly, the magnitude of the overall interference signal may be analysed. This is referred to as the output response, V, of the microscopy apparatus. Analysis of the phase of this signal would give additional information but this not always necessary. Oscillation of the magnitude of the overall interference signal with changes in the phase difference between them caused by defocussing of the sample may be analysed. When the sample is defocused, the lateral resolution achieved by analysing the oscillation of the magnitude of the overall interference signal is preferably in or around the range of 0.3 to 0.5 μm. Oscillation of the magnitude of the overall interference signal with changes in the phase difference between them caused by defocussing of the sample may be analysed to determine the optimum the value of defocus which gives the best contrast between features of the sample.

When a reference beam of radiation is used, the method may comprise using a microscopy apparatus which comprises a first sample irradiation arm and a second reference beam arm. An oil immersion objective lens may be provided in the first arm of the apparatus. A Bragg cell may be used in each arm, to effect frequency shifting of the radiation which passes through it. Preferably, a first Bragg cell introduces a frequency shift of, for example, 80 MHz and the second Bragg cell introduces a frequency shift of, for example, 80 MHz±1 kHz thus allowing the overall signal to be detected at the difference frequency 1 kHz. The use of two Bragg cells may reduce the effects of spurious reflections in the Bragg cells. The use of two Bragg cells may allow the overall signal to be detected at a convenient frequency, e.g. 1 kHz or 10 kHz. Such a microscopy apparatus may be described as a heterodyne interferometry microscopy apparatus. The method may comprise using a microscopy apparatus which comprises a photodetector whose output is detected and analysed in a lock-in amplifier and a PC. These may be used to detect and record the amplitude and phase of the detected radiation as a function of defocus, z.

According to a second aspect of the invention there is provided a microscopy apparatus which carries out the method according to the first aspect of the invention.

The microscopy apparatus may be a far field apparatus, i.e. the excitation of the surface waves and the detection of radiation generated by the surface waves is achieved from the far field.

The microscopy apparatus may comprise or be coupled to a radiation source, which produces the beam of radiation used to irradiate the sample.

The radiation source may comprise a laser. The laser may comprise a continuous wave laser, for example a 633 nm HeNe laser. The laser may comprise a pulsed laser, for example a titanium sapphire laser. Pulsed lasers are especially appropriate for use in multi-photon or harmonic systems.

The microscopy apparatus may comprise a lens through which the sample is irradiated by the beam of radiation. The lens may be a fluid immersion objective lens. The lens may be an oil immersion objective lens. The lens may be a Zeiss CP-Achromat 100×/1.25oil oil immersion objective lens. The lens may comprise other commercially available objective lens with sufficient numerical aperture to excite the desired surface waves. The lens may have a numerical aperture (NA) of 1.25, or greater than 1.5 for example 1 65. For high numerical aperture lenses, a high refractive index immersion fluid will be used. For example, for a lens having a numerical aperture of 1.65, the refractive index of the fluid in the lens may be approximately 1.78.

The microscopy apparatus may comprise expansion optics for the beam of radiation. These may comprise a beam expander. The microscopy apparatus may comprise one or more beam splitters. The microscopy apparatus may comprise one or more optical frequency shifters, for example Bragg cells.

The microscopy apparatus may comprise or be coupled to one or more radiation detectors. The microscopy apparatus may comprise one or more photodetectors. These may comprise one or more photodiodes and/or one or more photomultipliers, such as avalanche or vacuum photomultipliers. The microscopy apparatus may comprise one or more lock-in amplifiers. The signal produced by the or each detector may be filtered and/or amplified by one or more lock-in amplifiers.

The microscopy apparatus may comprise or be coupled to analysing means. The analysing means may be coupled to the or each or some of the radiation detectors, and may receive and analyse signals from the or each or some of the detectors. Additionally or alternatively, the analysing means may be coupled to the or each or some of the lock-in amplifiers, and may receive and analyse signals from the or each or some of the lock-in amplifiers. The analysing means may display the signal received from the or each or some of the detectors or the or each or some of the lock-in amplifiers. The analysing means may comprise a PC.

The microscopy apparatus may comprise a sample holder. This may support the sample. When the sample is a biological sample, the sample holder may support the sample in an aqueous environment.

The microscopy apparatus may comprise means for producing an annular beam of radiation, used to irradiate the sample. This may comprise a source of radiation which produces an annular beam of radiation. This may comprise the objective lens and a ring placed in the back focal plane of the lens. This may be positioned such that irradiation of the sample takes place over a range of angles which includes the range of angles for excitation of surface waves, but substantially excludes other angles.

The microscopy apparatus may comprise scanning means. This may allow the sample to be scanned to provide information about a number of points thereof. The scanning means may comprise mechanical scanning means. The mechanical scanning means may comprise one or more mechanical stages, which may move the sample in a raster scan. The scanning means may additionally or alternatively comprise mirror scanning means. These may be similar to that provided in commercially available confocal microscopes. When provided, the lens may be moved to scan the sample. The beam of radiation used to irradiate the sample may be moved to scan the sample. This may be achieved using mirror scanning means.

Alternatively, the microscopy apparatus may have a widefield configuration. This involves irradiating the sample over a range of angles, covering an extended area of the sample. Information about a number of points of the sample may therefore be obtained without the need to employ any scanning technique. The widefield microscopy apparatus may comprise a diffuser, which may be used to diffract the radiation used to irradiate the sample over a range of angles. The widefield microscopy apparatus may comprise interference means, which may be used to combine radiation from the sample and a reference beam of radiation. Alternatively, use of a reference beam may be dispensed with, and the apparatus may comprise means for changing the interference conditions between different parts of the radiation irradiating the sample. The apparatus may then comprise a conventional optical microscope with an oil illumination objective lens, with critical illumination of the sample. The apparatus may further comprise a filter for filtering the input distribution in the back focal plane of the apparatus. The apparatus may comprise a spatial light modulator in the back focal plane, which may be used to change the relative phase of the light incident close to normal incidence and that involved with excitation of surface waves. The SLM introduces different phase changes to different portions of the beam in order to optimise the contrast between different regions of the sample. The phase stepping algorithm could be applied to extract further quantative information. The apparatus may comprise a CCD camera or another camera of sufficient dynamic range. These may be used to detect the radiation generated by the surface waves.

The microscopy apparatus may comprise sample moving means, for varying the position of the sample off the focal plane of the microscopy apparatus, i.e. vary the defocus z of the sample. This is referred to as defocussing the sample. The sample moving means may vary the position of the sample off the focal plane of lens of the microscopy apparatus. The microscopy apparatus may comprise means for measuring the position of the sample off the focal plane of the microscopy apparatus, i.e. the defocus z.

When the surface waves which are excited comprise surface plasmons, the microscopy apparatus may comprise or be coupled to a polariser. The polariser preferably results in radiation used to irradiate the sample which is least substantially p-polarised in the plane of the sample surface and substantially s-polarised normal to this direction. The microscopy apparatus may comprise means for controlling the range of incident azimuthal angles of the radiation used to irradiate the sample, so that the incident s-polarised radiation is reduced.

When the detected radiation comprises radiation irradiated from the sample surface which has excited one or more surface plasmons therein and radiation irradiated from the sample surface which has not excited any surface plasmons therein, the microscopy apparatus may be provided with or configured as an interferometer to achieve interference of these radiations, provided that they are coherent with each other.

The analysing means of the microscopy apparatus may analyse the signal generated by the interference of these radiations to obtain information about the sample. The analysing means may analyse the magnitude of the signal generated by the interference of these radiations. The analysing means may analyse the oscillation of the magnitude of the signal generated by the interference of these radiations with changes in the phase difference between them caused by defocussing of the sample.

When the signal generated by the combination of the radiation irradiated from the sample surface which has excited one or more surface plasmons therein and the radiation irradiated from the sample surface which has not excited any surface plasmons therein is to be combined with a reference beam of radiation, the microscopy apparatus may comprise or be coupled to a reference beam source. The microscopy apparatus may comprise a single source of radiation, which may produce the beam of radiation for irradiating the sample and the reference beam of radiation. These radiations may be produced by using, for example, a beam splitter. The microscopy apparatus may be provided with or configured as an interferometer to achieve interference of the signal and The reference beam of radiation.

The analysing means may analyse the overall signal generated by the interference of the above signal and the reference beam of radiation, to obtain information about the sample. The analysing means may analyse the magnitude of the overall signal. The analysing means may analyse the oscillation of the magnitude of the overall signal with changes in the phase difference between them caused by defocussing of the sample.

When a reference beam of radiation is used, the microscopy apparatus may comprise a first sample irradiation arm and a second reference beam arm. An oil immersion objective lens may be provided in the first arm of the apparatus. A Bragg cell may be provided in each arm, to effect frequency shifting of the radiation which passes through it.

When the detected radiation includes fluorescent radiation from the sample, the microscopy apparatus may comprise a detector which detects one or more characteristics of this radiation. The detector may detect the number and/or the energy spectrum of the fluorescent photons. A proportion of the beam of radiation used to irradiate the sample may be reflected from the sample surface. The fluorescent radiation from the sample may be weaker than this reflected radiation.

The microscopy apparatus may comprise blocking means for at least partially blocking radiation reflected from the sample. The blocking means may comprise an interference filter.

According to another aspect the invention comprises software, possibly encoded on a machine-readable data carrier, which when loaded into a processor of a computer-controlled analyser causes the method of the invention to be performed.

An embodiment of the invention will now be described, by way of example only, with reference to the accompanying drawings, in which.

Figure 1:
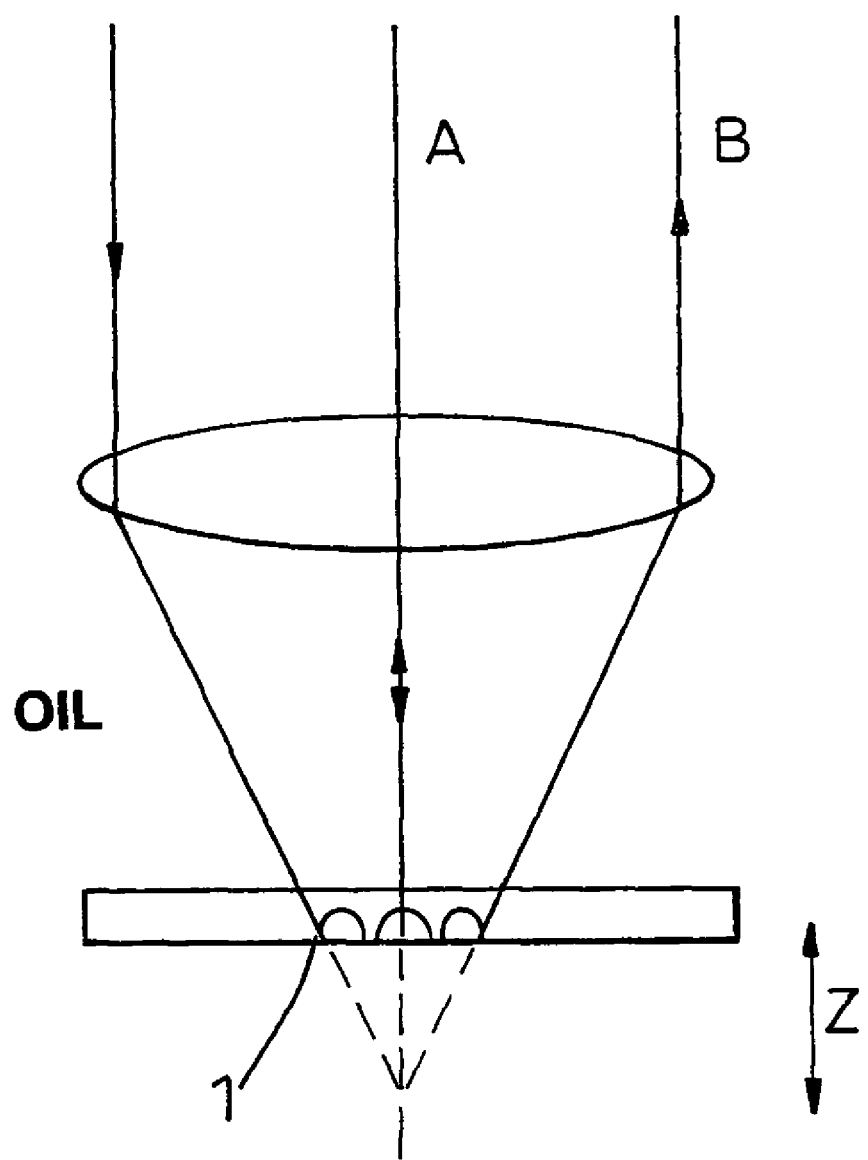
FIG. 1 shows a schematic diagram of a beam of radiation transmitted through an oil immersion lens and incident on a sample which is defocused.

FIG. 1 shows the situation when a beam of radiation is transmitted through an oil immersion lens and irradiates a sample which is placed off the focal plane of the lens. The sample comprises a metal coated glass coverslip. When the sample is above the focal plane, as shown, a circle of radiation will be incident on the sample surface, and as surface plasmons are excited by radiation incident on the sample at a particular range of angles, only an annulus of the circle of radiation will excite surface plasmons. These will propagate along the sample surface, depicted by line 1, and come to a focus at the centre of the annulus. Reciprocity considerations mean that energy continuously leaks back into the oil immersion lens as the SPs propagate, so that surface plasmon radiation returns through the lens along path B and this radiation is detected. When the defocus z of the sample is varied, the phase difference between the radiation travelling along paths A and B changes. Combining the radiation from paths A and B with each other and with a common reference beam, will give an overall interference signal the magnitude of which (V(z)) will oscillate as the phase between paths A and B changes. The periodicity of this interference signal will be equal to the change in defocus necessary for the relative phase between the two paths to change by $2\pi$ radians. The periodicity, $\Delta z$ of the oscillations in the V(z) signal can be readily shown to be equal to:

$$\Delta z = \frac{\lambda}{2n(1-\cos\theta_p)} \quad (1)$$

where $\lambda$ is the wavelength of the beam of radiation in vacuum, n is the refractive index of the oil in the oil immersion lens (assumed equal to that of the coverslip), $\theta_p$ is the angle of incidence of the radiation used to irradiate the sample which excites surface plasmons. This will change when a dielectric is deposited on the metal coating.

Figure 2:
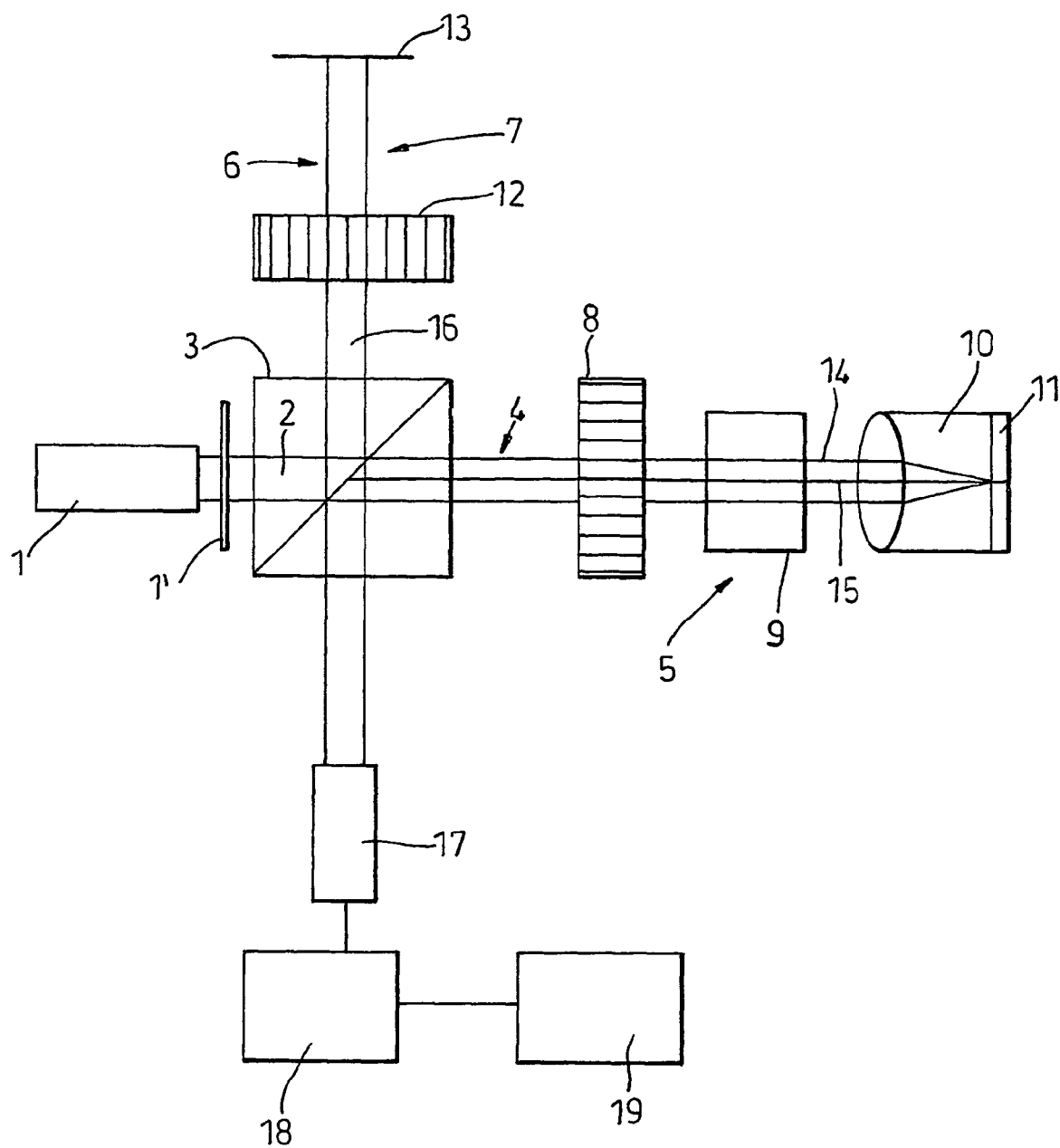
FIG. 2 shows a schematic diagram of a first embodiment of the microscopy apparatus according to the second aspect of the invention.

FIG. 2 shows a schematic diagram of one embodiment of a microscopy apparatus 1 of the invention. This comprises a scanning heterodyne interferometer microscopy apparatus. The apparatus comprises a 633 nm HeNe laser radiation source 1, and a polariser 1'. A beam of radiation 2 from the laser 1 is incident on a beam splitter 3, where it is split into a first beam of radiation 4 which travels along a sample irradiation arm 5 of the apparatus, and a second beam of radiation 6 which travels along a reference beam arm 7 of the apparatus. The sample irradiation arm comprises a first Bragg cell 8, a beam expander 9, and an oil immersion objective lens 10 which abuts a sample 11. The lens is a Zeiss CP-Achromat 100×/1.25oil oil immersion objective lens, with a numerical aperture (NA) of 1.25. The refractive index of the oil is 1.52. The sample is held in a sample holder (not shown), attached to sample moving means (not shown) which acts to move the sample to various positions off the focal plane of the lens 10, i.e. acts to vary the defocus z of the sample. The reference beam arm 7 comprises a second Bragg cell 12 and a mirror 13.

The beam of radiation 4 passes through the Bragg cell 8, the beam expander 9 and the lens 10, and is incident on the sample 11. The beam of radiation will contain a mixture of p-polarised and s-polarised radiation. When the radiation is linearly polarised in the back focal plane of the apparatus, there will be equal average intensities of p and s polarised radiation which will vary with the azimuthal angle of the beam of incident radiation. Varying the input polarisation and spatial distribution in the back focal plane allows the balance between the two polarisation states to be controlled.

The annulus of radiation incident on the sample surface which generates surface plasmons is incident at approximately 45 degrees to the normal when the sample is backed with air. These propagate along the sample surface and come to a focus at the centre of the lens 10. Radiation 14 is irradiated from the sample surface which has excited one or more surface plasmons therein, and radiation 15 is irradiated from the sample surface which has not excited any surface plasmons therein.

The second beam of radiation 6 travels along the reference beam arm 7 and passes through the second Bragg cell 12 and is incident on the mirror 13. A beam of radiation 16 is reflected from the mirror 13, and travels back along the reference beam arm through the Bragg cell 12 and is incident on the beam splitter 3. The beam of radiation 16 acts as a reference beam of radiation.

The Bragg cell 8 introduces a frequency shift of 80 MHz±1 kHz in the signal generated by the interference of radiations 14 and 15, and the Bragg cell 13 introduces a frequency shift of 80 MHz in the beam of radiation 16. The use of two Bragg cells reduces the effects of spurious reflections therein.

The radiations 14 and 15 and the reference beam of radiation 16 are combined in the beam splitter 3 which acts as an interferometer. This produces an overall signal which, because of frequency shifting of the Bragg cells, can be detected at the difference frequency of 1 kHz. The overall signal is passed to a detector 17 which detects the amplitude and phase of the overall signal. The signal from the detector 17 is passed to a lock-in amplifier 18, which filters and amplifies the signal The signal from the amplifier 18 is passed to analysing means comprising a PC 19. Analysis of the overall signal provides information about the sample 11.

Figure 3:
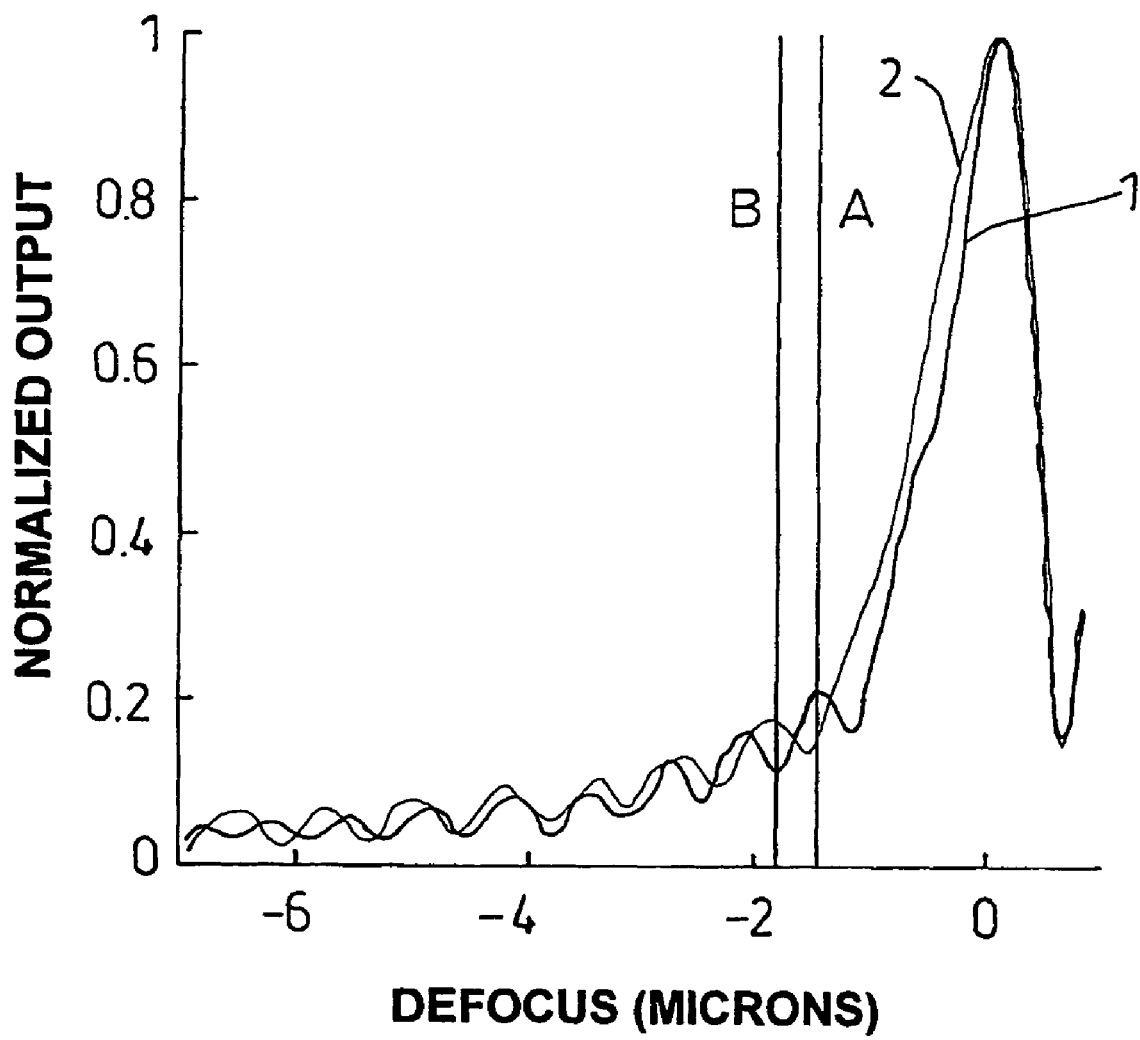
FIG. 3 shows the measured modulus of the oscillation of the magnitude of the overall signal with variation of the defocus z of a first sample (line 1), and a second sample (line 2)

FIG. 3 shows the measured modulus of the oscillation of the magnitude of the overall signal with variation of the defocus z of two samples. Note that negative defocus denotes moving the sample towards the focal plane of the objective lens 10. Line 1 was obtained from a first sample comprising a glass coverslip coated with an approximately 1 nm layer of chromium overcoated with an approximately 50 nm layer of gold, and line 2 was obtained from a second sample comprising a glass coverslip coated with an approximately 1 nm layer of chromium overcoated with an approximately 50 nm layer of gold and an approximately 20 nm layer of silicon dioxide deposited on the gold. The glass of the coverslips was chosen such that the refractive index thereof was almost the same as the refractive index of the oil of the lens 10.

The results show a characteristic ripple pattern, which arises from the excitation of the surface plasmons. The periodicity of the ripple of line 1 is 761 nm, which is extremely close to the value of 758 nm predicted from equation (1) above. The periodicity of line 2 is 676 nm, again close to the value of 672 nm predicted from equation (1). From the lines 1 and 2 it can be seen that when the samples are placed at the focal plane of the lens very little contrast between the samples would be expected. However, when the samples are moved towards the objective lens 10, the first sample will first appear bright compared to the second sample, see, for instance, defocus A on FIG. 3. For larger defocuses the contrast will reverse, at, for instance, defocus B.

Figure 4A:
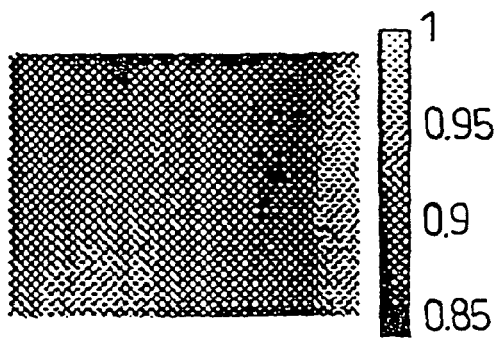
FIG. 4 shows images obtained by mechanically scanning a sample with
 (a) the image obtained with the sample at a defocus z of substantially 0 μm;
 (b) the image obtained with the sample at a defocus z of −1.5 μm, and
 (c) the image obtained with the sample at a defocus z of −1.85 μm.
Figure 4B:
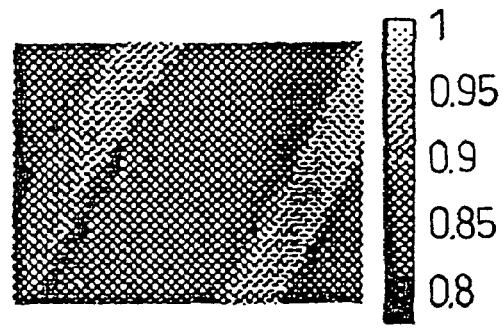
Figure 4C:
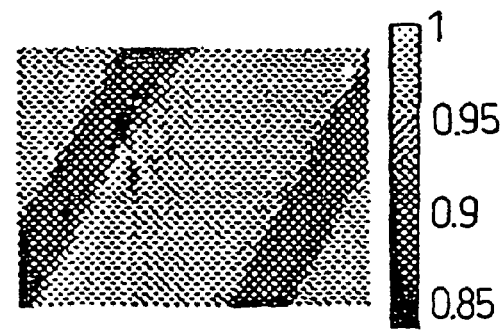

The series of images in FIG. 4 were obtained by mechanically scanning a sample comprising a glass coverslip coated with an approximately 1 nm layer of chromium overcoated with an approximately 50 nm layer of gold and an approximately 20 nm layer of silicon dioxide deposited on the gold etched away leaving 2 µm wide stripes of bare gold followed by 6 µm wide stripes of dielectric coated gold. The images shown in FIGS. 4a, 4b and 4c were obtained by scanning the objective lens 10 over the sample. FIG. 4a was obtained with the sample close to the focal plane of the lens 10, and shows barely discernible contrast between the different stripes as expected. FIG. 4b was obtained at a defocus z of the sample of −1.5 µm (A on FIG. 3), and shows bright bare gold stripes. FIG. 4c was obtained at a defocus z of −1.85 µm (B on FIG. 3), and shows dark bare gold stripes. Measurements from line traces extracted from the images show that the transition across the stripe interface is approximately 300 nm, indicative of diffraction limited rather than surface plasmon propagation length limited lateral resolution.

Figure 5:
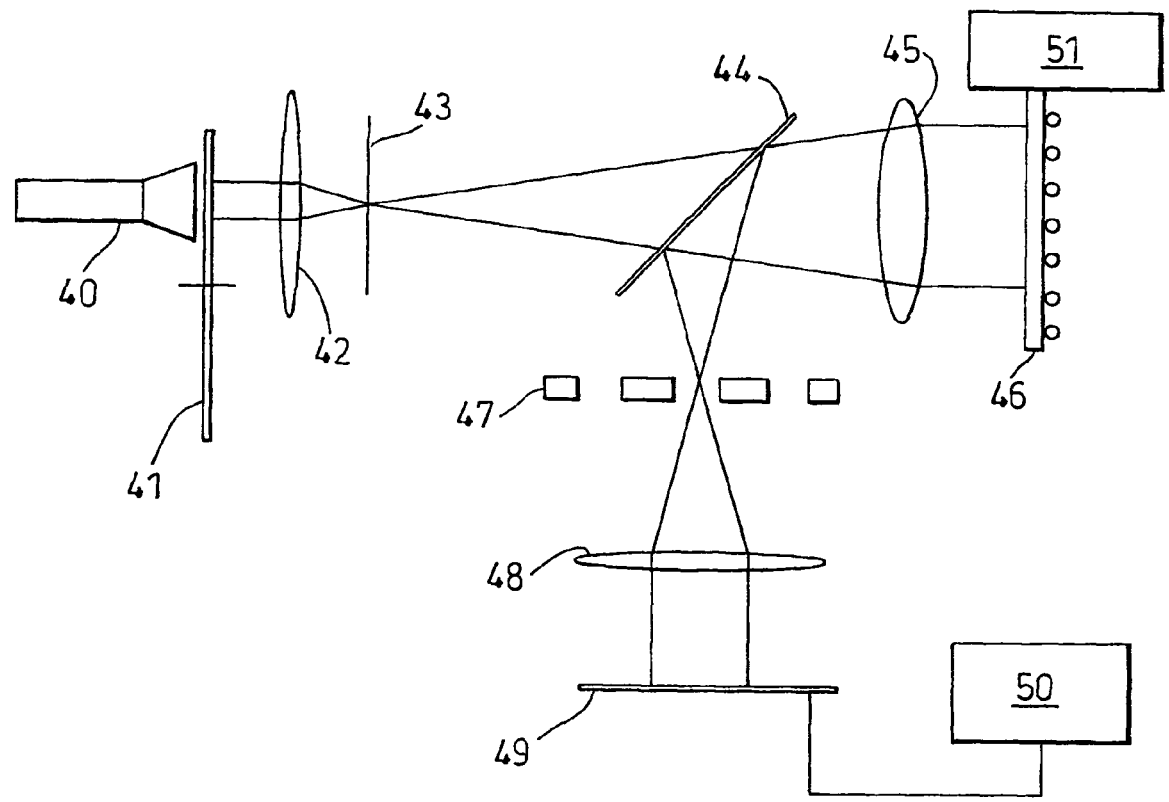
FIG. 5 shows another embodiment of the invention.

FIG. 5 shows another embodiment of the invention, with a wide field configuration. In the wide field configuration a beam of light from a light source such as a laser, 40, is passed to a rotating ground glass diffuser 41 placed in the image plane of the system. The light emerging from the diffuser is transformed by a transforming lens, 42, so that it encounters a spatial filter, 43, placed in the Fourier plane of the imaging system. This allows the different components of the illuminating beam to be changed in either amplitude or phase relative to each other. The beam is passed through a beamsplitter, 44 and the sample 46 is illuminated through an oil immersion objective, 45. The sample, 46, is thus illuminated with a range of angles which include angles which excite surface plasmons or optical surface waves. The light reflected from the sample is reflected back through the beamsplitter, 44, and a spatial light modulator, 47, is placed in the Fourier plane. This can alter the relative amplitude and phase of the reflected light (different regions of the SLM modifying the light differently). The light emerging from this is transformed by an additional lens 48 and detected on a light detecting device such as a CCD camera, 49. The output is passed to PC, 50, for processing and display. The phase relation between different portions of the beam may be further controlled by changing the focal position of the sample with the a sample-positioning device, depicted as 51.

It will be appreciated that in some embodiments defocusing the sample is extremely important since it allows the contributions from the surface plasmons to be varied and allows the contrast to particular features to be enhanced. Operating the interferometer in focus gives little contrast to surface plasmons. If the interferometer is to be used in focus it is advantageous to operate with an annular aperture to enhance the surface wave contribution. This is likely to give large sidelobes and poorer imaging performance. Furthermore, it does not allow one to "tune" the contrast by varying the defocus. Changing the separation between the sample and the objective lens makes the response very sensitive to the relative phase of beams A and B (in FIG. 1). This renders the system more robust and allows the propagation characteristics of the surface plasmons to be encoded as the amplitude of the interference signal (as well as the phase). This gives a precise measurement and imaging mode, which is not available when the sample is maintained in focus regardless of the type of illumination.

The invention claimed is:

1. A method of analyzing a sample using a microscopy apparatus comprising the steps of:
   (i) irradiating the sample with a beam of radiation in which at least some of the beam of radiation is incident on the sample at an angle or angles which results in the excitation of surface waves;
   (ii) exciting surface waves at a surface of the sample;
   (iii) confining the surface waves to an area having a principal dimension which is comparable to the wavelength of the surface waves by allowing the surface waves to come to a focus;
   (iv) detecting radiation which includes radiation produced by the surface waves; and
   (v) analyzing the detected radiation to obtain information about the sample.

2. A method according to claim 1 wherein said surface waves are excited over a substantially circular or elliptical area of said sample surface, and are allowed to come to a focus at substantially the center of said area.

3. A method according to claim 2 wherein excitation over the substantially circular or elliptical area is achieved by said sample at the focal plane of said microscopy apparatus.

4. A method according to claim 1 wherein said surface waves are excited over an annulus of said sample surface, and are allowed to come to a focus at substantially the center of said annulus.

5. A method according to claim 4 where excitation over an annulus is achieved by placing said sample at a position off the focal plane of said microscopy apparatus.

6. A method according to claim 5 wherein said position of the sample off the focal plane of said microscopy apparatus is varied to determine an optimum defocus at which said sample is positioned for analysis.

7. A method according claim 1 which comprises a far field method, wherein excitation of said surface waves and said detection of radiation generated by said surface waves is achieved from the far field.

8. A method according to claim 7 wherein said sample is scanned using scanning means to provide information about a number of points thereof.

9. A method according to claim 1 wherein said microscopy apparatus has a widefield configuration.

10. A method according to claim 9 which further comprises the steps of: passing a beam of radiation through a diffuser; using a resultant beam to irradiate said sample and a reference mirror each with a speckle pattern; causing the radiation from these to be interfered; and detecting the interference signal.

11. A method according to claim 10 which further comprises the steps of: changing the interference conditions between different parts of the radiation irradiating said sample; illuminating the sample; and coherently adding radiations generated by the excitation of surface waves.

12. A method according claim 1 wherein said sample comprises a conducting material with one or more dielectric materials deposited on or attached to a surface of said conducting material.

13. A method according to claim 12 wherein said sample comprises a metal layer with one or more dielectric materials deposited on or attached to a surface thereof, the metal layer being chosen to be at least substantially opaque to the radiation used to irradiate said sample and substantially transparent to fluorescent radiation from the sample.

14. A method according to claim 1 wherein two or more of the surface waves together produce fluorescence in the sample.

15. A method according to claim 14 characterized in that said detected radiation includes fluorescent radiation from said sample.

16. A method according to claim 14 wherein said sample has at least one fluorophore added to it and detected fluorescent radiation is affected by the presence of the fluorophore, and provides information about the sample.

17. A method according claim 14 which comprises at least partially blocking radiation reflected from the sample.

18. A method according claim 1 comprising exciting harmonic surface waves.

19. A method according to claim 18 comprising detecting radiation produced by said harmonic surface waves.

20. A method according to claim 19 wherein radiation produced by said harmonic surface waves is combined with a reference beam of radiation.

21. A method according to claim 20 wherein said radiations are combined by causing them to interfere with each other, using an apparatus provided with or configured as an interferometer.

22. A method according to claim 1 wherein said surface waves excited are surface plasmons.

23. A method according to claim 22 wherein said detected radiation includes radiation irradiated from said sample surface which has excited surface plasmons therein and radiation irradiated from said sample surface which has not excited any surface plasmons therein.

24. A method according to claim 23 wherein at least one characteristic of the detected radiation is analyzed, the characteristic comprising the phase and/or amplitude of the radiation.

25. A method according to claim 23 wherein said radiation irradiated from said sample surface which has excited surface plasmons therein and the radiation irradiated from said sample surface which has not excited any surface plasmons therein are combined with a reference beam of radiation by allowing them to interfere with each other, and an overall interference signal generated by interference of the combined radiations and the reference beam of radiation is analyzed to obtain information about said sample.

26. A method according to claim 25 performed by using a microscopy apparatus which comprises a first sample irradiation arm and a second reference beam arm.

27. A method of analyzing a sample using a microscopy apparatus having a widefield configuration comprising the steps of:
(i) passing a beam of radiation through a diffuser and using a resultant beam to irradiate said sample and a reference mirror with a respective speckle pattern, at least some of said radiation being incident on said sample at an angle or angles which results in the excitation of surface waves;
(ii) exciting surface waves at a surface of the sample;
(iii) confining the surface waves to an area having a principal dimension which is comparable to the wavelength of the surface waves by allowing the surface waves to come to a focus;
(iv) interfering radiation produced by the surface waves and radiation from the reference mirror and detecting the interference signal; and
(v) analyzing the detected interference signal to obtain information about the sample.

28. Microscopy apparatus comprising:
(i) an incident beam emitter;
(ii) a sample holder;
(iii) a sample-emitted radiation detector adapted to produce a detection signal;
(iv) a signal analyzer adapted to analyze the detected signal;
wherein, said incident beam emitter is arranged to provide at least some of a beam of radiation incident on the sample at one or more angles which results in the excitation of surface waves at a surface of the sample, the apparatus being arranged to confine the surface waves to an area having a principle dimension which is comparable to the wavelength of the surface waves by allowing the surface waves to come to a focus;
wherein said radiation detector is arranged to detect radiation which includes radiation produced by the surface waves; and
wherein said signal analyzer is arranged to analyze the detected radiation to obtain information about the sample.

29. An apparatus according to claim 28 which comprises a far field apparatus, excitation of said surface waves and detection of radiation generated by said surface waves being achievable from the far field.

30. An apparatus according to claim 28 comprising a radiation source which produces the beam of radiation used to irradiate the sample.

31. An apparatus according to claim 28 comprising a laser and a fluid immersion objective lens through which the sample is irradiated by the laser.

32. An apparatus according claim 28 which comprises scanning means which allow the sample to be scanned to provide information about a number of points thereof.

33. An apparatus according to claim 28 which has a widefield configuration and which in use irradiates the sample over a range of angles, covering an extended area for the sample, and obtains information about a number of points of the sample without the need to employ a scanning technique.

34. An apparatus according to claim 33 wherein said apparatus comprises a diffuser which is used to diffract the radiation used to irradiate the sample over a range of angles.

35. An apparatus according to claim 33 wherein said apparatus comprise interference means, which are used to combine radiation from the sample and a reference beam of radiation.

36. An apparatus according to claim 33 wherein means is provided to change the interference conditions between different parts of the radiation irradiating the sample.

37. An apparatus according claim 28 comprising sample moving means for varying the position of the sample off the focal plane of the microscopy apparatus.

38. An apparatus according to claim 28 wherein a polarizer is provided.

39. An apparatus according to claim 28 wherein an interferometer is provided to interfere radiation coming from an area of the sample which generates surface plasmon—generated fluorescence with other radiation.

40. Microscopy apparatus comprising:
(i) an incident beam input;
(ii) a sample holder;
(iii) a sample-emitted radiation detector adapted to produce a detection signal;
(iv) a signal analyzer adapted to analyze the detected signal;
wherein the incident beam input is adapted to cause a beam of radiation to impact upon the sample positioned in use at said sample positioning area, and said detector is adapted to detect radiation emitted from said sample due to the action of incident beam-induced surface plasmons; and
wherein said beam input and sample holder are configured such that at least some of the incident beam is incident upon the sample in use at an angle such as to generate surface plasmons; and
wherein said apparatus further has:
a first arm for irradiating said sample with a laser beam and for gathering radiation from first regions of the sample which have surface plasmons excited therein and from second regions of the sample which do not have surface plasmons excited therein,
said first arm having an interference means adapted to cause the radiation from the first and second regions to interfere so as to produce a signal beam;
a second arm for producing a reference lower beam; and
an interferometer for interfering said reference beam and said signal beam,
wherein said detector is positioned to detect the beam caused by the interference of said signal and reference beams.

41. Microscopy apparatus comprising:
(i) an incident beam input;
(ii) a sample holder;
(iii) a sample-emitted radiation detector adapted to produce a detection signal;
(iv) a signal analyzer adapted to analyze the detected signal;
wherein the incident beam input is adapted to cause a beam of radiation to impact upon the sample positioned in use at said sample positioning area, and said detection is adapted to detect radiation emitted from said sample due to the action of incident beam-induced surface plasmons; and
wherein said beam input and said sample holder are configured such that at least some of the incident beam is incident upon the sample in use at an angle such as to generate surface plasmons; and
wherein said apparatus further has:
a first arm for irradiating said sample with a laser beam and for gathering radiation from first regions of the sample which have surface plasmons excited therein and form second regions of the sample which do not have surface plasmons excited therein,
said first arm having an interference means adapted to cause the radiation from the first and second region to interfere so as to produce a signal beam;
a second arm for producing a reference lower beam; and an interferometer for interfering said reference beam and said signal beam,
wherein said detector is positioned to detect the beam caused by the interference of said signal and reference beams; and
wherein the first arm has a first Bragg cell disposed in the path of radiation emitted from the sample, and the second arm has Bragg cell disposed on the path of the reference beam, the Bragg cell introducing the same frequency shift in the radiation that encounters them.

* * * * *